US012582688B2

(12) United States Patent
van Staden et al.

(10) Patent No.: US 12,582,688 B2
(45) Date of Patent: Mar. 24, 2026

(54) COMPOSITIONS FOR THE TREATMENT OF HYPOPIGMENTATION

(71) Applicant: University of Pretoria, Pretoria (ZA)

(72) Inventors: Analike Blom van Staden, Pretoria (ZA); Namrita Lall, Pretoria (ZA)

(73) Assignee: University of Pretoria, Pretoria (ZA)

( * ) Notice: Subject to any disclaimer, the term of this patent is extended or adjusted under 35 U.S.C. 154(b) by 300 days.

(21) Appl. No.: 18/574,200

(22) PCT Filed: Jun. 28, 2022

(86) PCT No.: PCT/IB2022/055989
§ 371 (c)(1),
(2) Date: Dec. 26, 2023

(87) PCT Pub. No.: WO2023/275740
PCT Pub. Date: Jan. 5, 2023

(65) Prior Publication Data
US 2024/0285710 A1 Aug. 29, 2024

(30) Foreign Application Priority Data
Jun. 28, 2021 (GB) ...................................... 2109297

(51) Int. Cl.
| | |
|---|---|
| *A61K 36/00* | (2006.01) |
| *A61K 9/00* | (2006.01) |
| *A61K 36/48* | (2006.01) |
| *A61K 47/10* | (2017.01) |
| *A61K 47/14* | (2017.01) |
| *A61K 47/26* | (2006.01) |
| *A61K 47/32* | (2006.01) |
| *A61P 17/00* | (2006.01) |

(52) U.S. Cl.
CPC ............ *A61K 36/48* (2013.01); *A61K 9/0014* (2013.01); *A61K 47/10* (2013.01); *A61K 47/14* (2013.01); *A61K 47/26* (2013.01); *A61K 47/32* (2013.01); *A61P 17/00* (2018.01); *A61K 2236/33* (2013.01)

(58) Field of Classification Search
CPC ...................................................... A61K 36/48
See application file for complete search history.

(56) References Cited

U.S. PATENT DOCUMENTS

| | | |
|---|---|---|
| 2008/0247974 A1 | 10/2008 | Gruner-Richter et al. |
| 2017/0056309 A1* | 3/2017 | Marini .................. A61Q 19/02 |

FOREIGN PATENT DOCUMENTS

| | | |
|---|---|---|
| GB | 2562302 A | 11/2018 |
| JP | H06128121 A | 5/1994 |

OTHER PUBLICATIONS

International Search Report mailed on Jul. 11, 2022 in PCT/IB2022/055989.
Written Opinion mailed on Jul. 11, 2022 in PCT/IB2022/055989.
Blom van Staden A et al., "Medicinal plants for Progressive Macular Hypomelanosis," 2015, South African Journal of Botany, vol. 98, p. 172.
Blom van Staden A et al., "The Effect of Aspalathus linearis (Burm.f.) R.Dahlgren and its compounds on tyrosinase and melanogenesis," 2021, Scientific Reports, vol. 11, 7020.
Blom van Staden A et al., "Potential Medicinal plants for Progressive Macular Hypomelanosis," 2017, South African Journal of Botany, vol. 111, pp. 346-357.

* cited by examiner

*Primary Examiner* — Qiuwen Mi
(74) *Attorney, Agent, or Firm* — Fox Rothschild LLP

(57) ABSTRACT

The present invention relates to a topical composition comprising a 100 µg/mL ethanolic extract from the plant *Aspalathus linearis* together with a dermatologically acceptable carrier for use in a method of preventing or treating a hypopigmentary disorder of skin in a subject comprising applying the topical composition to the skin of the subject. The invention further relates to methods of preventing or treating a hypopigmentary disorder of skin in a subject comprising applying the topical composition to the skin of the subject.

12 Claims, 6 Drawing Sheets

COMPOSITIONS FOR THE TREATMENT OF HYPOPIGMENTATION

CROSS-REFERENCE TO RELATED APPLICATIONS

This application is the U.S. national phase of International Patent Application No. PCT/IB2022/055989, filed on Jun. 28, 2022, which claims priority to United Kingdom Patent Application No. 2109297.8, filed on Jun. 28, 2021, the disclosures of which are incorporated herein by reference in their entirety.

BACKGROUND OF THE INVENTION

The present invention relates to the use of a composition comprising an extract from the plant *Aspalathus linearis* in preventing or treating hypo-pigmented disorders of the skin. The invention also relates to methods of preventing or treating hypo-pigmented disorders of the skin using compositions comprising an extract from the plant *Aspalathus linearis*.

Hypopigmentation disorders, a problem faced worldwide, are due to reduced melanin production in the melanocytes and often due to the obstruction of melanosome transfer. A reduction in melanogenesis is generally due to decreased tyrosinase activity, lack of melanin precursors and reduced expression of the genes regulating melanogenesis. Microfibrils and particular receptors within melanocyte dendrites are required for the transfer of melanosomes from melanocytes to keratinocytes. Hypopigmentation, therefore, occurs concurrently with a decrease in the rate of melanosome transfer.

Hypopigmentary disorders can either be genetic, as is the case with albanism, or acquired. Examples of acquired hypopigmentated disorders are idiopathic guttate hypomelanosis, *Pityriasis alba*, progressive macular hypomelanosis, post-inflammatory hypopigmentation, leukoderma and vitiligo. Irrespective of the familiarity of the aforementioned diseases, pigmentation disorders remain challenging to treat. The prevalence of hypopigmentation ranges from 0.06 to 2.28%, with an average of 1% worldwide, this accounts for 76 000 000 people. The hypopigmented lesions in *Pityriasis alba* patients have been shown to develop due to reduced melanin transfer from the melanocytes to the keratinocytes and an increase in damaged melanocytes.

Current treatments for hypopigmentation diseases include surgical based therapies, phototherapy and steroidal therapies; however, each treatment is associated with side effects. For example, short-term use of corticosteroids has resulted in headaches, electrolyte abnormalities, viral infection, pancreatitis, hypertension, skin atrophy, perioral dermatitis, rosacea, purpura, acne, delayed wound healing, hypertrichosis, pigmentation alterations and exacerbation of skin infections, and hematologic and neuropsychologic effects. In addition, although UV radiation is not harmful, overexposure to UV may lead to increased skin aging, and the development of melanomas and squamous cell cancers. Further, many of the current treatments for hypopigmentary disorders primarily focus on the reduction of melanin production, but few studies are aimed at stimulating melanin production in areas where there is a lack of pigment.

The present invention is aimed at determining how *Aspalathus linearis* (Burm.f.) R. Dahlgren (Fabaceae) could aid in the regulation of melanin production and melanin transfer for hypopigmentary disorders.

*A. linearis* is a woody shrub that belongs to the Fabaceae family. *A. linearis*, commonly known as Rooibos, is endemic to the Western Cape in South Africa. Rooibos tea has been traditionally used for medicinal purposes for numerous years. The popularity and utilisation of *A. linearis* has since progressed from being limited to a herbal tea to the use in cosmeceutical products, nutraceuticals and as extracts used in beverages and food. More than 80% of *A. linearis* produced is exported and is currently sold in more than 37 countries in the world.

SUMMARY OF THE INVENTION

The present invention relates to topical compositions comprising of or consisting of a 100 µg/mL ethanolic extract from the plant *Aspalathus linearis* together with a dermatologically acceptable carrier for use in a method of preventing or treating a hypopigmentary disorder of skin in a subject comprising applying the topical composition to the skin of the subject. The invention also relates to methods of preventing or treating a hypopigmentary disorder of skin in a subject comprising applying the topical composition to the skin of the subject.

In a first aspect of the invention there is provided for a topical composition comprising of or consisting of a 100 µg/mL ethanolic extract from the plant *Aspalathus linearis* and dermatologically acceptable carrier for use in a method of preventing or treating a hypopigmentary disorder of skin in a subject, the method comprising applying the topical composition to the skin of the subject.

It will be appreciated that the topical composition comprises a 100 µg/mL ethanolic extract from the plant *Aspalathus linearis*, acrylates/$C_{10-30}$ alkyl acrylate crosspolymer, glycerin, caprylic/capric triglyceride, isopropyl myristate, dicaprylyl carbonate, acrylate/acrylamide copolymer dispersed in oil and polysorbate-85, a phenoxyethanol and ethylhexylglycerin preservative blend, water, and a dermatologically acceptable carrier.

In a first embodiment of the invention the ethanolic extract from the plant *Aspalathus linearis* is a crude extract.

In a second embodiment of the invention the topical composition is a lotion, cream, gel, serum, or emulsion.

In a third embodiment of the invention the topical composition may comprise or consist of one or more additive selected from the group comprising of or consisting of a rheology modifier, a suspending agent, a thickener, a denaturant, a humectant, a solvent, an emollient, an emulsifier and/or a preservative.

In a fourth embodiment of the invention the topical composition comprises or consists of the following:
   a) 100 µg/mL crude ethanolic extract from the plant *Aspalathus linearis;*
   b) acrylates/$C_{10-30}$ alkyl acrylate crosspolymer, preferably 1 to 10 mg/ml acrylates/$C_{10-30}$ alkyl acrylate crosspolymer;
   c) glycerin, preferably 10 to 50 mg/mL glycerin;
   d) caprylic/capric triglyceride, preferably 25 to 100 mg/mL caprylic/capric triglyceride;
   e) isopropyl myristate, preferably 5 to 50 mg/mL isopropyl myristate;
   f) dicaprylyl carbonate, preferably 5 to 50 mg/mL dicaprylyl carbonate;
   g) acrylate/acrylamide copolymer dispersed in oil and polysorbate-85, preferably 5 to 15 mg/mL acrylate/acrylamide copolymer dispersed in oil and polysorbate-85;

h) a phenoxyethanol and ethylhexylglycerin preservative blend, preferably 5 to 15 mg/mL a phenoxyethanol and ethylhexylglycerin preservative blend; and i) water.

In a fourth embodiment of the invention the hypopigmentary disorder is selected from the group consisting of or comprising of idiopathic guttate hypomelanosis, *Pityriasis alba*, progressive macular hypomelanosis, post-inflammatory hypopigmentation, leukoderma, vitiligo and hypopigmented scarring.

In a preferred embodiment of the invention the topical composition stimulates melanin production and/or melanin transfer.

In a second aspect of the invention there is provided for a method of preventing or treating a hypopigmentary disorder of skin in a subject comprising applying a topical composition to the skin of the subject, wherein the topical composition comprises a 100 μg/mL ethanolic extract from the plant *Aspalathus linearis*, and a dermatologically acceptable carrier.

It will be appreciated that the topical composition comprises a 100 μg/mL ethanolic extract from the plant *Aspalathus linearis*, acrylates/$C_{10-30}$ alkyl acrylate crosspolymer, glycerin, caprylic/capric triglyceride, isopropyl myristate, dicaprylyl carbonate, acrylate/acrylamide copolymer dispersed in oil and polysorbate-85, a phenoxyethanol and ethylhexylglycerin preservative blend, water, and a dermatologically acceptable carrier.

In a first embodiment of the second aspect of the invention the ethanolic extract from the plant *Aspalathus linearis* is a crude extract.

In a second embodiment of the second aspect of the invention the topical composition is a lotion, cream, gel, serum, or emulsion.

In a third embodiment of the second aspect of the invention the topical composition may comprise or consist of one or more additive selected from the group comprising of or consisting of a rheology modifier, a suspending agent, a thickener, a denaturant, a humectant, a solvent, an emollient, an emulsifier and/or a preservative.

In a fourth embodiment of the second aspect of the invention the topical composition comprises or consists of the following:

a) 100 μg/mL crude ethanolic extract from the plant *Aspalathus linearis;* b) acrylates/$C_{10-30}$ alkyl acrylate crosspolymer, preferably 1 to 10 mg/ml acrylates/$C_{10-30}$ alkyl acrylate crosspolymer;

c) glycerin, preferably 10 to 50 mg/mL glycerin;

d) caprylic/capric triglyceride, preferably 25 to 100 mg/mL caprylic/capric triglyceride;

e) isopropyl myristate, preferably 5 to 50 mg/mL isopropyl myristate;

f) dicaprylyl carbonate, preferably 5 to 50 mg/mL dicaprylyl carbonate;

g) acrylate/acrylamide copolymer dispersed in oil and polysorbate-85, preferably 5 to 15 mg/mL acrylate/acrylamide copolymer dispersed in oil and polysorbate-85;

h) a phenoxyethanol and ethylhexylglycerin preservative blend, preferably 5 to 15 mg/mL a phenoxyethanol and ethylhexylglycerin preservative blend; and i) water.

In a fifth embodiment of the second aspect of invention the hypopigmentary disorder is selected from the group consisting of or comprising of idiopathic guttate hypomelanosis, *Pityriasis alba*, progressive macular hypomelanosis, post-inflammatory hypopigmentation, leukoderma, vitiligo and hypopigmented scarring.

In a preferred embodiment of the second aspect of the invention the topical composition stimulates melanin production and/or melanin transfer.

In a third aspect of the invention there is provided for a topical composition comprising of or consisting of a 100 μg/mL ethanolic extract from the plant *Aspalathus linearis*, acrylates/$C_{10-30}$ alkyl acrylate crosspolymer, glycerin, caprylic/capric triglyceride, isopropyl myristate, dicaprylyl carbonate, acrylate/acrylamide copolymer dispersed in oil and polysorbate-85, a phenoxyethanol and ethylhexylglycerin preservative blend, water, and a dermatologically acceptable carrier.

In a first embodiment of the third aspect of the invention the ethanolic extract from the plant *Aspalathus linearis* is a crude extract.

In a second embodiment of the third aspect of the invention the topical composition is a lotion, cream, gel, serum, or emulsion.

In a third embodiment of the third aspect of the invention the topical composition may comprise or consist of one or more additive selected from the group comprising of or consisting of a rheology modifier, a suspending agent, a thickener, a denaturant, a humectant, a solvent, an emollient, an emulsifier and/or a preservative.

In a fourth embodiment of the third aspect of the invention the topical composition comprises or consists of the following:

a) 100 μg/mL crude ethanolic extract from the plant *Aspalathus linearis;* b) acrylates/$C_{10-30}$ alkyl acrylate crosspolymer, preferably 1 to 10 mg/ml acrylates/$C_{10-30}$ alkyl acrylate crosspolymer;

c) glycerin, preferably 10 to 50 mg/mL glycerin;

d) caprylic/capric triglyceride, preferably 25 to 100 mg/mL caprylic/capric triglyceride;

e) isopropyl myristate, preferably 5 to 50 mg/mL isopropyl myristate;

f) dicaprylyl carbonate, preferably 5 to 50 mg/mL dicaprylyl carbonate;

g) acrylate/acrylamide copolymer dispersed in oil and polysorbate-85, preferably 5 to 15 mg/mL acrylate/acrylamide copolymer dispersed in oil and polysorbate-85;

h) a phenoxyethanol and ethylhexylglycerin preservative blend, preferably 5 to 15 mg/mL a phenoxyethanol and ethylhexylglycerin preservative blend; and i) water.

BRIEF DESCRIPTION OF THE FIGURES

Non-limiting embodiments of the invention will now be described by way of example only and with reference to the following figures.

DETAILED DESCRIPTION OF THE INVENTION

Figure 1:
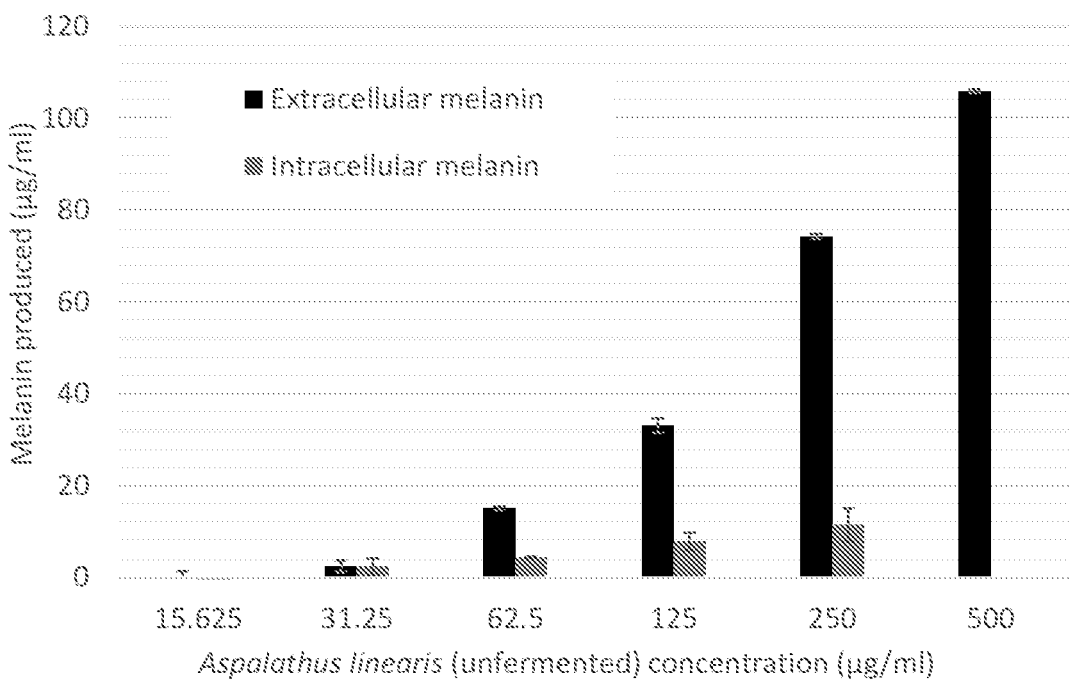
FIG. 1: The effect of *Aspalathus linearis* and the positive control (theophylline) on melanin production (intracellular and extracellular) in B16-F10 mouse melanocytes compared with untreated cells.
Figure 1:
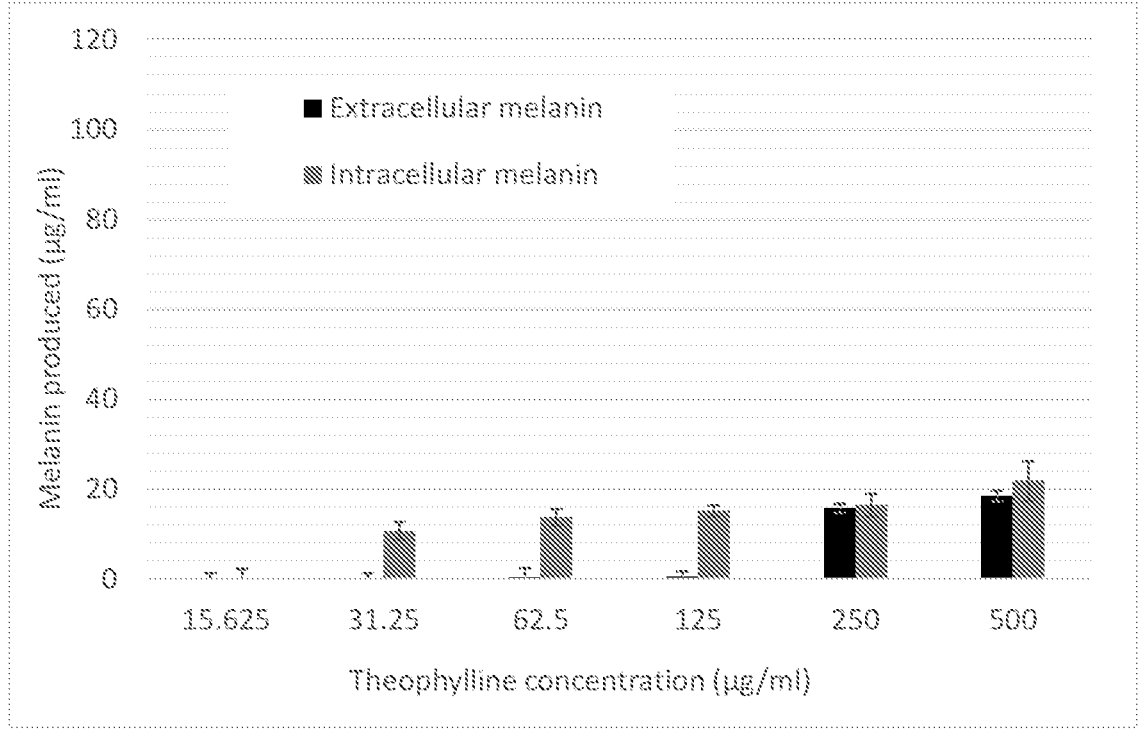

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

In its broadest form the invention relates to a composition comprising an extracts derived from *A. linearis*. The composition displays activity for the stimulation of melanin production and/or melanin transfer. The composition is useful for preventing or treating a hypopigmentary disorder of the skin in a subject.

Melanogenesis is the synthesis of melanin, in the form of pigment granules called melanosomes, and occurs in the melanocytes. Melanin transfer occurs as soon as the melanin produced in the melanocytes has reached maturity and moved to the tip of the dendrites. Melanin transfer occurs naturally within the cell as was noticeable in the untreated cells, but could be influenced (induced or inhibited) by other treatments with compounds and plant extracts.

The Applicant has found that extracts of *A. linearis* stimulate melanin production. The melanin production stimulated by the composition comprising an extract of *A. linearis* according to the present invention may be due to the presence of aspalathin (a phytoestrogen similar to glycyrrhizin), quercetin—which plays a key role in modulation of melanogenesis—and cytokinins (plant hormones), which increase the levels of tyrosinase. The small amount of melanin present intracellularly in comparison to the large amount of melanin present extracellularly in the cells treated with *A. linearis* may indicate an increase in melanin transfer.

The stimulation of melanin production and melanin transfer by compositions comprising an extract of *A. linearis* according to the present invention may provide an alternative treatment for hypopigmentation disorders, especially in cases of reduced pigmentation in particular those that are due to a reduction in melanin production or a hindrance in melanin transfer. A plant-based composition, with low cytotoxicity, provides a safer alternative to current treatments.

The extract of *A. linearis* exhibits a negligible effect on cellular proliferation of human melanoma cells (UCT-Mel1) with 50% cell viability concentrations higher than 200 μg/mL, indicating low to no toxicity. The ethanolic extract of *A. linearis* has further been shown not to be mutagenic. In addition, the ethanolic extract of *A. linearis* was identified as a non-irritant. Compositions of the present invention comprising the ethanolic extract of *A. linearis* have been shown to be stable at all storage conditions. Moreover, compositions of the present invention comprising the ethanolic extract of *A. linearis* at a concentration of 100 μg/mL in finished formulation resulted in significant repigmentation of 21% in the non-pigmented zones compared to the pigmented zones, which was observed in 88% of the volunteers in a clinical study.

It will be understood that the composition of the invention may be in the form of a pharmaceutical or cosmeceutical composition. The composition may be administered to a subject prior to a symptomatic state associated with hypopigmentary disorders, or after a symptomatic onset of hypopigmentary disorders in the subject.

Those skilled in the art will appreciate that there are a number of methods for synthesizing extracts from crude plant material. These methods include, among others, cutting, chopping, macerating and/or grinding raw plant material in at least one solvent in order to obtain a plant extract. It will also be appreciated that the crude plant material may be fresh material or dry plant material.

The solvent may be an organic solvent. Organic solvents typically used in the preparation of plant extracts include ethanol, methanol, butanol dichloromethane, chloroform, acetone and/or mixtures thereof. In one embodiment, the organic solvent is ethanol.

As used herein the term "crude extract" refers to a concentrated preparation of a plant extract obtained by removing secondary metabolites from the crude plant material with the aid of a suitable solvent. This may be done, for example, by submerging the crude plant material in the suitable solvent, removing the solvent and consequently evaporating all or nearly all of the solvent. As used herein the term "purified extract" refers to an extract obtained by separating the constituent parts of the crude extract from each other. By way of a non-limiting example, the constituent parts of the crude extract may be separated from one another by separating the polar constituents from the non-polar constituents. In so doing the active polar and/or non-polar constituents may thus be concentrated.

As described herein the composition of the present invention is a composition suitable for topical use on a subject. The subject may include a living animal, preferably a mammal and most preferably a human.

The composition may include a dermatologically acceptable vehicle, carrier and/or diluent. The pharmaceutical composition of the invention containing the extract may be in a form suitable for topical use. Suitable forms of the pharmaceutical composition include, for example, gels, lotions, creams, essences, toners, emulsions, soaps, shampoos, rinses, cleansers, solutions, ointments, jellies or suspensions. In one embodiment of the invention, the composition may be a topical composition in the form of a lotion, cream, gel, serum, or emulsion.

The "suitable forms" of the pharmaceutical composition may be combined with "pharmaceutically acceptable carriers" and other elements known in the art to produce creams, gels and lotions for use for general skin care. The pharmaceutical composition may further be combined with other ingredients which promote absorption by the skin.

The extract may be formulated as a pharmaceutical composition by methods known to those skilled in the art. Pharmaceutically acceptable ingredients may be used. The term "pharmaceutically acceptable" refers to properties and/or substances which are acceptable for administration to a subject from a pharmacological or toxicological point of view. Further "pharmaceutically acceptable" refers to factors such as formulation, stability, patient acceptance and bioavailability which will be known to a manufacturing pharmaceutical chemist from a physical/chemical point of view.

By "pharmaceutically acceptable carrier" is meant a solid or liquid filler, diluent or encapsulating substance which may be safely used for the administration of the pharmaceutical composition to a subject. The compositions of the invention may further include additives which enhance the properties of the composition. Examples of such additives include, but are not limited to rheology modifiers, suspending agents, thickeners, denaturants, humectants, solvents, emollients, emulsifiers and preservatives.

The use of the compositions containing the extract entails administration of an effective amount of the pharmaceutical composition containing the extract to a subject in order to prevent or treat a condition. The term "effective amount" in the context of preventing or treating a condition refers to the administration of an amount of the active plant extract to an individual in need of treatment, either a single dose or several doses of the pharmaceutical composition containing the extract.

In some embodiments, the effective amount is a concentration in the range of about 100 µg/mL to about 300 µg/mL of the crude extract in the composition, such as about 100 µg/mL, about 150 µg/mL, about 200 µg/mL, about 250 µg/mL, or about 300 µg/mL of extract in the composition. Preferably the effective amount of the crude extract in the composition is about 100 µg/mL.

Although some indications have been given as to suitable dosages of the extract and/or pharmaceutical composition containing the extract, the exact dosage and frequency of administration of the effective amount will be dependent on several factors. These factors include the individual components used, the formulation of the pharmaceutical composition containing the extract, the condition being treated, the severity of the condition, the age, weight, health and general physical condition of the subject being treated, and other medication that the subject may be taking, and other factors as are known to those skilled in the art.

The following examples are offered by way of illustration and not by way of limitation.

Example 1

Plant Material and Extract Preparation

Dried plant material of *A. linearis* was obtained from Rooibos Ltd. (GPS coordinates: S 32° 11.131' EO 18° 53.291') in Clanwilliam. A herbarium voucher specimen (PRU: 122176) was deposited at the H.G.W.J. Schweickerdt Herbarium, University of Pretoria, South Africa. The coarsely ground (0.4 mm) plant material (13.85 kg) was extracted with 34 L of EtOH. The ethanolic extract of *A. linearis* (ALEtOH) was filtered with a Buchner funnel (Whatman No. 3 filter paper), concentrated using a rotary evaporator at 40° C. and freeze-dried to a fine powder. The percentage yield of the freeze-dried extract was 9.03% of the dried plant material.

Example 2

Melanin Production

The amount of melanin produced in B16-F10 mouse melanocytes, after the treatment with the *A. linearis* and the positive control, theophylline, was determined by using the method described by Hill (Matsuda, et al., 2004). Cultured B16F10 mouse melanocytes (passage number 6) were trypsinized (0.25% trypsin and 0.1% EDTA at 37° C. for 5-10 min). Cells ($2 \times 10^4$ cells/well in 1.9 ml of MEM) were inoculated into 24-well plates using a pipette (FALCON 353046, Becton Dickinson Labware, NJ, U.S.A.), and incubated for 24 hours at 37° C. in the $CO_2$ incubator. After 24-hour incubation, 100 µl of each sample solution was added to each well in duplicate, and the 24-well plate was incubated for 72 hours at 37° C. in the $CO_2$ incubator. The ethanolic extract of *A. linearis* (concentrations ranging between 3.13 and 500 µg/ml) and the positive control-theophylline (concentrations ranging between 15.63 and 500 µg/ml) were dissolved in DMSO. A 0.5% DMSO concentration was used as a negative control. After incubation, the cultured medium was removed, and assayed for extracellular melanin. The cultured medium was centrifuged (900 g, 20 min at 4° C.) to give a supernatant. One millilitre of a mixture of 0.4 M HEPES buffer (pH 6.8) and EtOH (9:1, v/v) was added to 1 ml of the supernatant was separated. The OD at 475 nm of the resulting solution was measured, and the amount of extracellular melanin was determined. The remaining melanocytes were digested by the addition of 400 ml of 1 N NaOH, washed with 100 ml of CMF-D-PBS and trypsinized (0.25% trypsin and 0.1% EDTA at 37° C. for 5 to 10 min), and then incubated for 16 hours at room temperature. Spectrophotometric analysis of the amount of intracellular melanin was then performed at 475 nm.

The amount of melanin produced in the B16-F10 mouse melanocytes was determined spectrophotometrically. The cells treated with unfermented *A. linearis* exhibited a significant increase in the concentration of melanin present extracellularly, with no significant increase of melanin present intracellularly. The B16F10 cells treated with 500 µg/ml (highest concentration tested) unfermented *A. linearis* resulted in an additional 105 µg/ml (0 µg/ml intracellularly and 105 µg/ml extracellularly) of melanin produced than in the untreated cells, while theophylline, the positive control, only resulted in an additional 40 µg/ml (21 µg/ml intracellularly and 19 µg/ml extracellularly) of melanin formation. Therefore, *A. linearis* was significantly more active than theophylline (FIG. 1).

Example 3

Melanin Transfer

Primary human melanocytes and primary human keratinocytes were cultured in normal Dulbecco's Modified Eagle's Medium (DMEM) containing melanocyte and keratinocyte growth factors respectively. Melanocytes ($2.5 \times 10^3$ cells/well) were seeded on gelatine treated round coverslips in 24 well plates and were incubated at 37° C. for 72 hours. After the 72 hours the melanocyte medium was removed and medium (with a higher Ca concentration and keratinocyte growth factors) containing the keratinocytes ($25 \times 10^3$ cells/well) was added to each well. The co-culture was incubated overnight to ensure that the keratinocytes attached. The extract of *A. linearis* was added to the co-culture at concentrations ranging between 20 µg/ml and 80 µg/ml and incubated at 37° C. for 24 hours. The positive control alpha melanocyte stimulating hormone (α-MSH) was added to the cells at a concentration of $1.7 \times 10^5$ µg/ml (100 mM) and incubated at 37° C. for 24 hours. After 24 hours the treated cells and untreated cells were analysed with immunofluorescence (Cardinali, et al., 2008).

The 24-hour co-cultured cells were washed with PBS and fixed with MeOH (added at a temperature of −20° C.) and incubated for 4 minutes at −20° C. The fixed cells were washed with PBS to remove all the MeOH and incubated for 1 hour at room temperature with goat serum (0.5% in PBS) to remove effects of background noise. The coverslips were removed from the goat serum and placed on filter paper. Primary antibody staining consisted of anti-melanoma associated antigen (NKI/betab) at a ratio of 1:100 in PBS and anti-wide spectrum cytokeratin antibody at a ratio of 1:200 in PBS. Thirty microliters of primary antibody was added to each coverslip and incubated at room temperature for 1 hour. The coverslips were washed with PBS to remove any unbound antibodies. Thirty microliters of secondary antibodies, (Alexa 488 and Alexa 555) at a ratio of 1:500 in PBS, was added to the coverslips and incubated at room temperature for 1 hour and kept out of direct light. The coverslips were washed with PBS to remove any unbound antibodies and 300 to 500 µl of DAPI (4',6-diamidino-2-phenylindole) was added to stain the nuclei. The coverslips were incubated at room temperature for 5 min and washed with PBS. The washed coverslips were transferred to microscope slides containing mounting media and stored covered at 4° C., until analysed using the fluorescent microscope.

The statistical significance in the melanin transfer results obtained for the different treatments, was determined with a student's T-test. A P-value of P<0.05 was regarded as significant for all tests.

Figure 2:
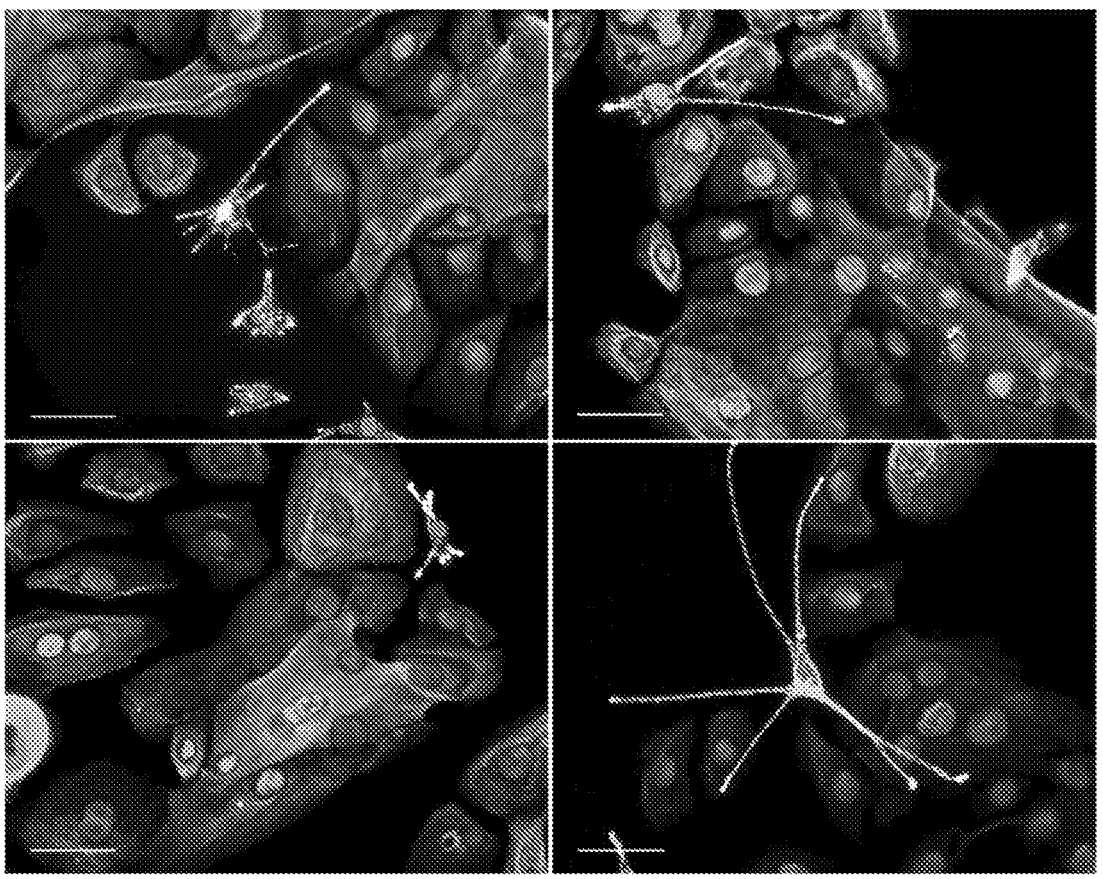
FIG. 2: Melanin transfer between the melanocytes or dendritic cells and keratinocytes (grey cells) in untreated cells. The nuclei of both types of cells were indicated by the round bodies present in the cells. Keratinocytes positive for melanin transfer have bright white dots (melanosomes) around their nuclei. The scale bar represents 10 μm.
Figure 3:
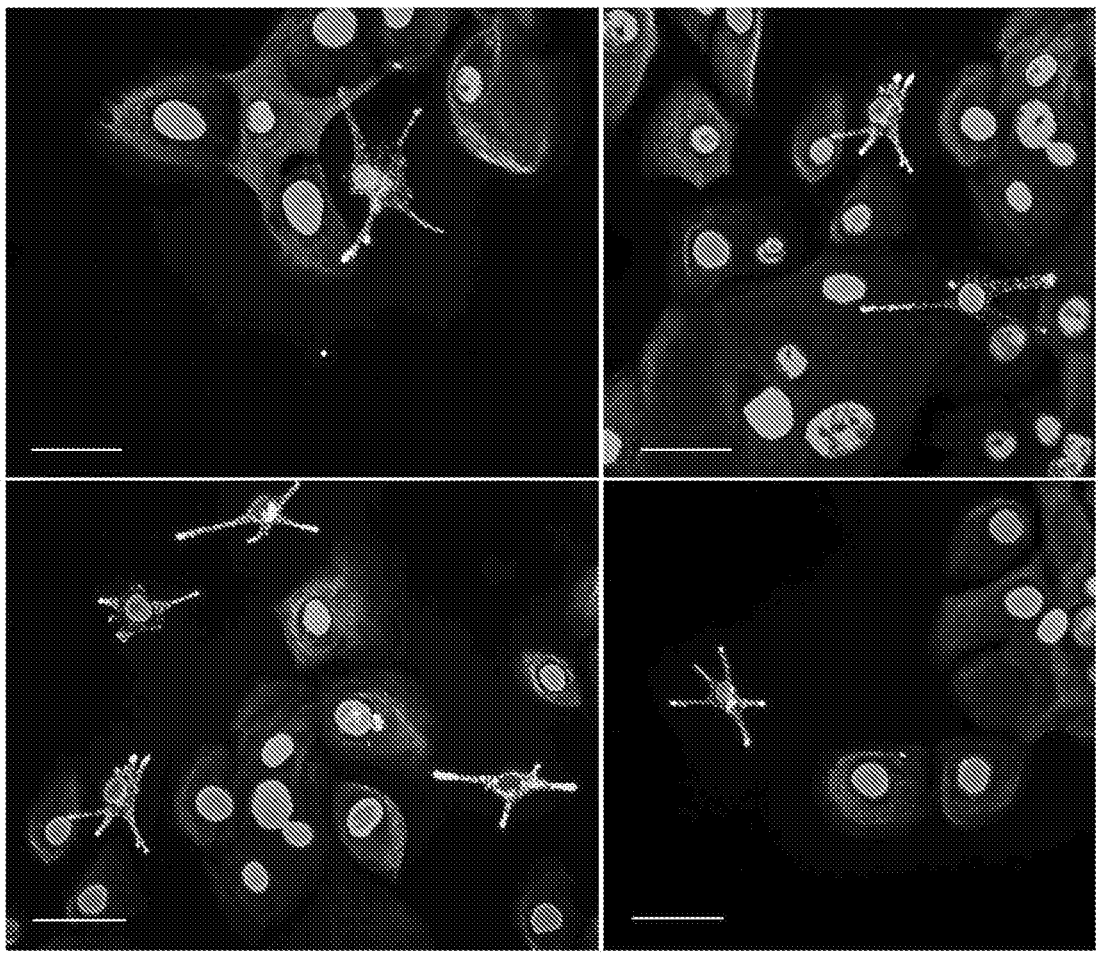
FIG. 3: Melanin transfer between the melanocytes-dendritic cells—and keratinocytes (grey cells) in cells treated with α-MSH. The nuclei of both type of cells were indicated by the round bodies present in the cells. Keratinocytes positive for melanin transfer have bright white dots (melanosomes) around their nuclei. The brighter white dendrite tips indicate a higher concentration of melanosomes present. The scale bar represents 10 μm.
Figure 4:
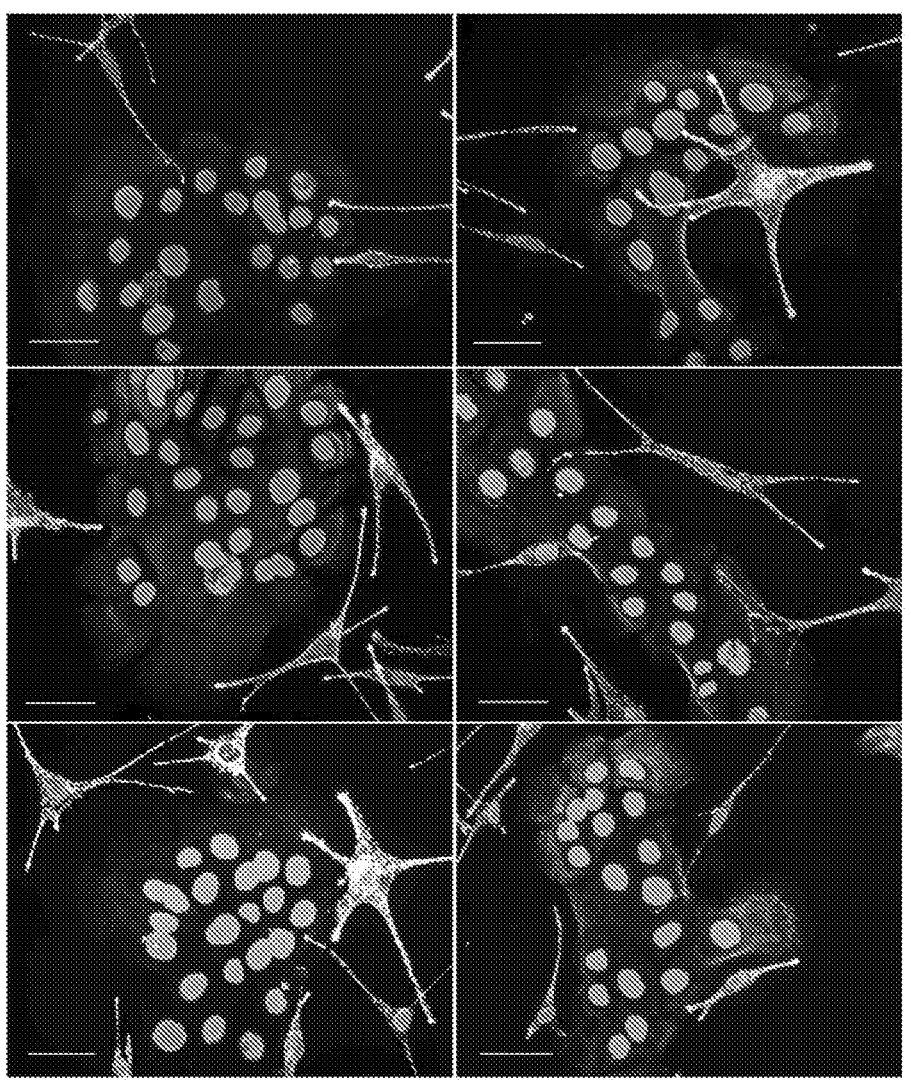
FIG. 4: Melanin transfer between the melanocytes-dendritic cells—and keratinocytes (grey cells) in cells treated with *A. linearis*. The nuclei of both type of cells were indicated by the round bodies present in the cells. Keratinocytes positive for melanin transfer have bright white dots (melanosomes) around their nuclei. The brighter white dendrite tips indicate a higher concentration of melanosomes present. The scale bar represents 10 μm.

Melanin transfer between normal human melanocytes (NHM) and normal human keratinocytes (NHK) was analysed by immunofluorescence. The cells treated with the positive control, alpha melanocyte stimulating hormone (α-MSH), showed a higher presence of melanosomes around the keratinocyte nuclei as observed in the untreated cells (FIGS. 2 and 3). After 24 hours of treatment, there was an increase in the fluorescence in the tip of the dendrites indicating increased amounts of melanin at these sites. The cells treated with *A. linearis* showed an increase in both melanocyte dendricity and the concentration of melanosomes present in the dendrite tips (FIG. 4). The treatment with *A. linearis* also led to an increased amount of positive keratinocytes with several melanosomes present around the nuclei of the keratinocytes.

Figure 5:
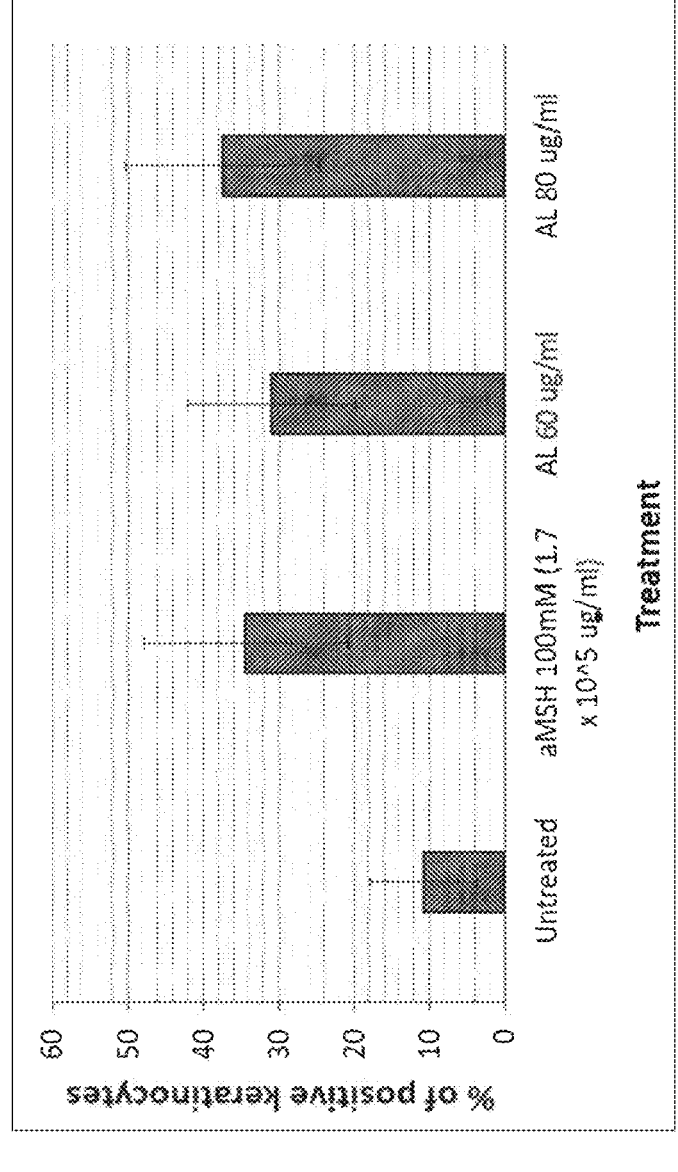
FIG. 5: Effect of *Aspalathus linearis* (AL) and α-MSH (positive control) on the amount of positive keratinocytes (melanosomes present around the nucleus of the keratinocytes) indicating melanin transferred compared to the untreated cells.

A quantitative comparison of the means of positive keratinocytes (melanin present around the nuclei) between the untreated cells and cells treated with α-MSH (100 mM) and *A. linearis* (60 µg/ml and 80 µg/ml) were conducted (FIG. 5). The results were statistically analysed with a Student's T-test and one way ANOVA (Tukey's Multiple Comparison Test), to determine whether the difference between the results obtained were significant (Table 1).

TABLE 1

Statistical significance between the results obtained for melanin transfer after 24 hours of treatment.

| | T-test | | | One-way |
| | Calculated t-value | Critical T-value (95%) | Relationship of t and T | ANOVA P-value at 95% CI |
| Treatments | | | | |
|---|---|---|---|---|
| αMSH (100 mM or 1.7 × 10⁵ µg/ml) vs Untreated cells | $7.599 \times 10^{-6}$ | 1.771 | t ≪ T | P < 0.001 |
| A. linearis (60 µg/ml) vs Untreated cells | $3.168 \times 10^{-6}$ | 1.771 | t ≪ T | P < 0.001 |
| A. linearis (80 µg/ml) vs Untreated cells | $3.469 \times 10^{-7}$ | 1.771 | t ≪ T | P < 0.001 |
| A. linearis (60 µg/ml) vs αMSH | 0.442 | 1.771 | t < T | P > 0.05 |
| A. linearis (80 µg/ml) vs αMSH | 0.535 | 1.771 | t < T | P > 0.05 |
| A. linearis (60 µg/ml) vs A. linearis (80 µg/ml) | 0.128 | 1.771 | t < T | P > 0.05 |

A significant difference between the untreated cells and the treated cells (α-MSH, *A. linearis* (60 µg/ml, 80 µg/ml)) was obtained when analysed with the One-way ANOVA test, with a P-value smaller than 0.001 (probability of approximately 1 in $1 \times 10^6$ of obtaining the observed differences between the means by coincidence). The difference between the mean values of α-MSH and *A. linearis* (60 µg/ml and 80 µg/ml) were insignificant as the P-values were larger than 0.05, however, the concentration of α-MSH was much higher than the concentrations analysed for *A. linearis*. The difference between the mean values of *A. linearis* (60 µg/ml) and *A. linearis* (80 µg/ml) were insignificant as the P-values were larger than 0.05, therefore, both concentrations had similar effects on melanin transfer.

Example 4

Cytotoxicity and Mutagenicity of *Aspalathus Linearis*

The antiproliferative activity of an ethanolic extract of *Aspalathus linearis* ($AL_{EtOH}$) was determined on human melanoma cells (UCT-Mel1). The cells were maintained in Dulbecco's Modified Eagle's Medium (DMEM), supplemented with 10% fetal bovine serum (FBS) and 1% antibiotics (Penicillin-Streptomycin). Cells were seeded in 96-well plates (100 000 cells/mL) and incubated overnight at 37° C. in 5% CO2 to allow for attachment. Following incubation, the cells were treated with varying concentrations of the samples (1.56 to 200 µg/mL) and the positive control (actinomycin D, 0.0039 to 0.5 µg/mL) for 72 hours at 37° C. in 5% CO2. An untreated cell control and solvent control (DMSO 0.5%) were included in the experiment. Following incubation, 20 µL Presto blue reagent was added to all the wells, and the plates were further incubated for an additional 3 hours. The cell viability was determined by measuring the fluorescence at an excitation of 560 nm and emission of 590 nm using a Perkin Elmer VICTOR Nivo microplate reader. The concentration where 50% of the cell viability was inhibited was calculated by normalising the data to the untreated cell control.

The extract of *A. linearis* exhibited negligible effect on cellular proliferation with 50% cell viability concentrations higher than 200 µg/mL, indicating low to no toxicity.

The mutagenicity of an ethanolic extract of *A. linearis* was determined with Ames test using the *S. typhimurium* strain TA100. The tester strain (TA-100) used in this study was selected based on its accuracy in detecting various known mutagens and is one of the recommended strains by the pharmaceutical industry (Purves et al., 1995). Briefly, the bacteria were cultured in Oxoid Nutrient broth at 37° C. for 16 hours on a rotative shaker. This overnight culture (100 µl) was mixed with 2 mL of top agar (containing histidine-biotin), 100 µl test solution and 500 µl phosphate buffer. The mixture was poured onto the minimal agar plate and incubated for 37° C. for 48 hours. Following incubation, the number of revertant colonies (mutants) in each plate were counted. All cultures were prepared in triplicate, and the ethanolic extract of *A. linearis* was tested at three concentrations, 185.19 µg/mL, 18.20 µg/mL, and 1.85 µg/mL. The positive control, 4-nitroquinoline 1-oxide (4-NQO), was used at a concentration of 0.74 µg/mL. The number of revertants observed at the different tested concentration of the ethanolic extract of *A. linearis* was compared to that of the negative control (plate treated with $dH_2O$) and the solvent control (plate treated with 10% DMSO).

The plates did not have any visible differences, indicating a lack of toxicity towards the bacterial cells. The number of spontaneous revertants observed for the negative and solvent control, and the ethanolic extract of *A. linearis* was in all cases within normal limits (Mortelmans and Zeiger, 2000), indicating that the ethanolic extract of *A. linearis* is not mutagenic (Table 2). The similarity of the tested sample to the negative control indicated that the ethanolic extract of *A. linearis* was not toxic toward the bacteria at the concentration tested. This is in accordance with previous reports that both the fermented and unfermented aqueous extracts of *A. linearis* exhibited antimutagenic activity against aflatoxin B1 induced mutagenesis using *Salmonella typhimurium* (TA100) (Van der Merwe et al., 2006). The mutagenicity results together with the cytotoxicity results obtained in vitro confirmed that it was safe to proceed with an irritancy study on humans in clinical studies.

TABLE 2

The number of revertants (his– to his+) per plate
for the bacterium *Salmonella typhimurium* determined using
Ames test treated with the ethanolic extract of *Aspalathus linearis*
(Burm. f.) R. Dahlgren and tested in triplicate.

| Sample | Trial 1 | Trial 2 | Trial 3 | Average | T-test[d] |
|---|---|---|---|---|---|
| AL$_{EtOH}$ (185.19 µg/mL) | 87 | 89 | 99 | 92 | P > 0.05 |
| AL$_{EtOH}$ (18.20 µg/mL) | 115 | 137 | 110 | 121 | P > 0.05 |
| AL$_{EtOH}$ (1.85 µg/mL) | 101 | 110 | 138 | 116 | P > 0.05 |
| 4-Nitroquinoline N-oxide[a] (0.74 µg/mL) | 459 | 416 | 515 | 463 | P < 0.05 |
| Water[b] | 117 | 106 | 77 | 100 | N/A |
| 10% DMSO[c] | 107 | 88 | 105 | 100 | P > 0.05 |

[a]Positive control;
[b]untreated control;
[c]Solvent control;
[d]T-test was conducted between the samples and the negative control Example 5

Irritancy of *Aspalathus Linearis*

The ethanolic extract of *A. linearis* was submitted for patch testing. The sample was prepared to a concentration of 300 µg/mL (final concentration of the sample in formulation) in 60% EtOH and distilled water. The concentration of the extract was below the concentration (345.5±2.47 µg/mL) resulting in 50% cell viability determined in human melanocytes. The sample was transferred to 8 mm Finn Chambers on micropore tape, together with the positive control (a known irritant) and negative control (demineralised water), which were used in an occlusive patch testing. Visual assessments and colour photographs of the test sub-sites were made at 24, 48 and 72 hours. A rating system was used to classify the reactions observed according to the following scale: 0=no irritancy reaction toward the sample; 0.5=a minimal response; 1=mild erythema; 2=definite erythema, or uniform redness, itching or a burning response; 3=cases where swelling occurred; 4=burning redness, oedema, papules and bullae were observed. The different ratings provided a mean score for the samples. If the mean score (average plus standard deviation) of the samples has a similar score or falls below that of the negative control, the samples were considered a non-irritant. If the mean score of the samples falls above that of negative control but was lower than that of positive control, the sample is regarded as a mild irritant. If the mean score of the samples falls above that of the positive control the sample is considered an irritant.

Twenty individuals were recruited, of which 18 were Caucasian females and 2 Caucasian males. Seventeen of the individuals were over the age of 40 and 3 were under the age of 40, but older than 25 years of age. Seventeen of the individuals were a skin type II, two were a skin type I and one individual was a skin type I as identified using the Fitzpatrick Skin Type Scale. The procedure of patch test was verbally explained to the individuals, after which each of them signed a consent form and supplied their medical history.

The ethanolic extract, together with the positive control and negative control, was applied to the 20 individuals using a patch test. Following the 24-hour treatment period, the patches were removed, and the observation documented. Five of the 20 individuals experienced a minimal response towards the positive control after 48-hours (rating of 0.5), while seven of the 20 individuals experienced mild erythema towards the positive control after 48-hours (rating of 1). The average of the scoring system for the positive control was 0.93. Once a reaction has developed, the positive reactions persisted for several days.

The ethanolic extract of *A. linearis* and the negative control both had an average score of 0.23. Therefore, the ethanolic extract of *A. linearis* was identified as a non-irritant.

Example 6

Stability of *Aspalathus Linearis*

The stability of the extract, including in a formulation, was determined to establish its shelf life, which included the expiration date for the utilisation of the product after opening. The stability data provides the correct storing data for the clinical trials and indicates whether the product will remain stable throughout the trial period.

The ethanolic extract was re-dissolved in 60% EtOH and distilled water to a concentration of 6000 µg/mL, of which 5% was added to the finished formulation. The final concentration in formulation was similar to the bioactive concentration in vitro. The stability of the ethanolic extract of *A.*

*linearis* alone (6000 µg/mL) and in a formulation (300 µg/mL) was determined at four temperatures, namely 5° C., room temperature (25° C.), 40° C. and 50° C. The stability of the samples was determined by investigating the appearance, odour, pH measured at 25° C. and the density indicating either water loss (WL) or solid gain (SG) measured at 25° C. Furthermore, the viscosity of the formulation was determined at 25° C. The stability was determined over a period of 12 weeks and inspected at 1, 2, 4, 6, 8 and 12 weeks.

The formulation was prepared as follows: 10 g of Carbopol™ Ultrez 21 was dissolved in 4165 mL of dH₂O and mixed at a slow speed using a homogeniser. While the mixture was being stirred 100 g glycerine was added. Myritol™ 318 (250 g), isopropyl myristate (25 g), Cetiol™ CC (75 g) and Novemer™ EC-1 polymer (50 g) were mixed in a separate container and then added to the main mixture, while mixing with moderate agitation. Euxyl™ PE 9010 was slowly added to the mixture until a uniform gel-cream was obtained.

The appearance and odour of the samples were determined through sensory analysis. The variation in pH was determined using a pH meter suited for formulations. The PH meter was first calibrated at pH 2, pH 4 and pH 7, and thereafter the pH of the extract and the formulation was determined. The electrode was rinsed between samples with standard rinse aid. The density was measured using a Mettler PM4800 DeltaRange® scale and a Sheen 1501/100 Pyknometer (S283830). The Pyknometer measured precisely 100 mL of the sample and water. The density ($p_{sample}$)

of the sample, measured as g/mL, was determined with the following calculation, where $p_{water}$ indicates the density of water:

$$p_{sample} = \frac{\text{(Mass of pyknometer filled with sample)} - \text{(mass of clean, dry pyknometer)}}{\text{(Mass of pyknometer filled with water)} - \text{(mass of clean, dry pyknometer)}} \times p_{water}$$

The viscosity of the formulation was determined using a rotational viscometer at 10 rpm (Rotation Per Minute) and measured in centipoise (cP).

Figure 6:
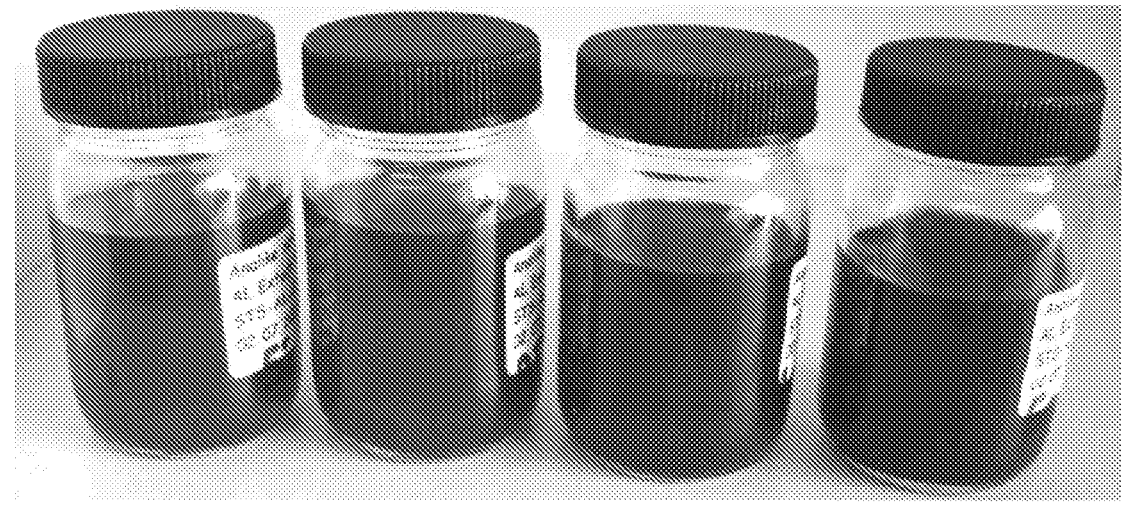
FIG. 6: The stability of the ethanolic extract of *Aspalathus linearis* (Burm.f.) R.Dahlgren determined over 12 weeks in glass jars. The amber brown liquid darkened at week 1 when stored at 40° C. and 50° C.
Figure 7:
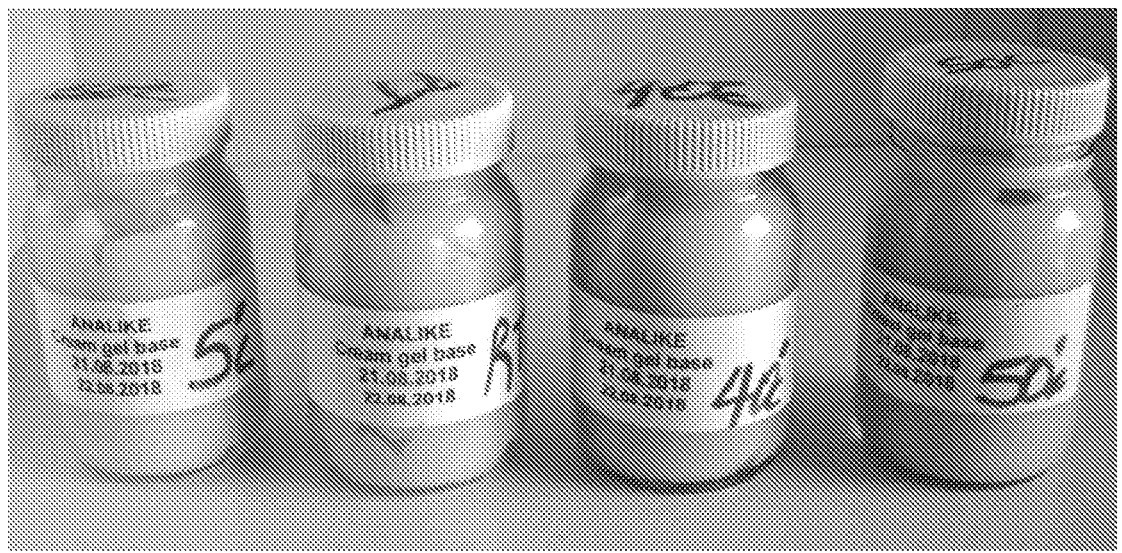
FIG. 7: The stability of the ethanolic extract of *Aspalathus linearis* (Burm.f.) R.Dahlgren, 5% in a cream gel formulation determined over 12 weeks in glass jars.

The appearance of the ethanolic extract of *A. linearis* alone and in formulation stayed a consistent amber-brown liquid and off white, thick, smooth gel-cream, respectively, at 5° C. over the 12 weeks (FIGS. 6 and 7). The ethanolic extract of *A. linearis* started to darken at week 6 when stored at 25° C., 40° C. and 50° C., while the formulation darkened at week 4 when stored at 25° C. and at week 1 when stored at 40° C. and 50° C. The colour change is possibly due to the oxidation and degradation of the phenolic compounds present in the extract. Phenolic compounds have been reported for their vast odour complexes in food, which changes depending on the different exposure to high temperatures. The initial odour of the ethanolic extract of *A. linearis* alone and in the formulation was similar to a herbal tea odour. This odour remained constant over the 12 weeks at the different concentrations tested for the formulation but became slightly stronger in the extract after 12 weeks at 40° C. and after 6 weeks at 50° C. (Table 3 and 4).

TABLE 3

The stability of the ethanolic extract of *Aspalathus linearis*
(Burm. f.) R. Dahlgren determined over 12 weeks in glass jars.

| Tests | Storage Conditions | Storage Intervals | | | | |
|---|---|---|---|---|---|---|
| | | 1 week | 2 weeks | 4 weeks | 8 weeks | 12 weeks |
| Appearance | 5° C. | Complies | Complies | Complies | Complies | Complies |
| Initial result: | 25° C. | Complies | Complies | Very slightly darker | Very slightly darker | Very slightly darker |
| Amber brown liquid | 40° C. | Complies | Complies | Slightly darker | Slightly darker | Slightly darker |
| | 50° C. | Complies | Complies | Darker | Darker | Darker |
| Odour | 5° C. | Complies | Complies | Complies | Complies | Complies |
| Initial result: | 25° C. | Complies | Complies | Complies | Complies | Complies |
| Herb tea | 40° C. | Complies | Complies | Complies | Complies | Complies |
| | 50° C. | Complies | Complies | Slightly stronger | Slightly stronger | Stronger |
| pH at 25° C. | 5° C. | 4.54 | 4.80 | 4.85 | 4.67 | 5.04 |
| Initial result: | 25° C. | 4.64 | 4.65 | 4.69 | 5.67 | 5.03 |
| 4.44 | 40° C. | 4.20 | 4.68 | 4.62 | 4.44 | 4.87 |
| | 50° C. | 4.31 | 4.53 | 4.49 | 4.36 | 4.63 |
| SG at 25° C. | 5° C. | 0.955 | 0.923 | 0.943 | 0.927 | 0.926 |
| Initial results: | 25° C. | 0.950 | 0.940 | 0.944 | 0.946 | 0.942 |
| 0.951 g/mL | 40° C. | 0.938 | 0.917 | 0.945 | 0.948 | 0.948 |
| | 50° C. | 0.932 | 0.920 | 0.942 | 0.947 | 0.949 |

TABLE 4

The stability of the ethanolic extract of *Aspalathus linearis* (Burm. f.) R.
Dahlgren, 5% in a cream gel formulation determined over 12 weeks in glass jars.

| Tests | Storage Conditions | Storage Intervals | | | | |
|---|---|---|---|---|---|---|
| | | 1 week | 2 weeks | 4 weeks | 8 weeks | 12 weeks |
| Appearance | 5° C. | Complies | Complies | Complies | Complies | Complies |
| Initial result: | 25° C. | Complies | Complies | Very slightly darker | Slightly darker/ peachy | Dark peachy colour |
| Off white, thick smooth | | | | | | |
| gel cream | 40° C. | Off white/ peachy | Slightly darker | Slightly darker | Slightly darker | Slightly darker |
| | 50° C. | Off white/ peachy | Darker | Darker | Darker | Darker |
| Odour | 5° C. | Complies | Complies | Complies | Complies | Complies |
| Initial result: | 25° C. | Complies | Complies | Complies | Complies | Complies |
| Characteristic | 40° C. | Complies | Complies | Complies | Complies | Complies |
| | 50° C. | Complies | Complies | Complies | Complies | Complies |
| pH at 25° C. | 5° C. | 6.59 | 5.92 | 6.42 | 5.75 | 6.13 |
| Initial result: 6.12 | 25° C. | 6.32 | 6.22 | 6.28 | 5.91 | 6.23 |
| | 40° C. | 6.21 | 6.37 | 6.02 | 5.97 | 6.02 |
| | 50° C. | 6.16 | 6.16 | 6.18 | 5.90 | 6.07 |
| Viscosity at 25° C. | 5° C. | 46 500 | 47 000 | 47 000 | 45 500 | 44 000 |
| Spindle: 6 @ 10 rpm | 25° C. | 48 800 | 48 400 | 46 600 | 47 500 | 45 600 |
| Factor: 1000 | 40° C. | 46 700 | 45 900 | 43 500 | 44 600 | 42 400 |
| Initial results: 53 000 cps | 50° C. | 45 600 | 43 500 | 42 000 | 40 200 | 32 500 |
| SG at 25° C. | 5° C. | N/R | N/R | 0.962 | 0.967 | 0.971 |
| Initial results: 0.966 g/mL | 25° C. | N/R | N/R | 0.962 | 0.971 | 0.969 |
| | 40° C. | N/R | N/R | 0.971 | 0.971 | 0.967 |
| | 50° C. | N/R | N/R | 0.971 | 0.976 | 0.977 |

N/R = Not required

No significant changes in the pH and density of the samples were observed over the 12-week analysis period. An initial drop in viscosity was found, this initial drop is due to depolymerisation expected of formulations prepared using a high-shear mixer. After that, the formulation stayed stable at all temperatures, except at 50° C. The formulation had a significant drop (39%) in viscosity at 12 weeks. A decrease in viscosity at such high temperature was expected as elevated storage conditions can have a considerable effect on the stability of the polymers in the formulation. The results indicated that samples were stable at all storage conditions.

Example 7

Clinical Studies of *Aspalathus Linearis* Preparation

The ethanolic extract of *A. linearis* in a finished formulation (5%) was submitted to Dermscan Eurofins, a French company, for clinical studies. The clinical studies were conducted at Insight Research Laboratories in Mauritius. The clinical study was conducted on 30 individuals (ages ranged from 20 to 60 years) having a skin phototype of I to VI, with the majority having V or VI Fitzpatrick skin types. The study included subjects with localized depigmented areas on face, limbs and other parts of the body.

The individuals (both male and female) were divided into three groups, the first group received the placebo, the second group received the ethanolic extract of *A. linearis* at a concentration of 100 μg/mL in the finished formulation and the third group received the ethanolic extract of *A. linearis* at a concentration of 200 μg/mL in the finished formulation. The samples were prepared as described in Example 6 above. Briefly, 10 g of Carbopol Ultrez 21 was dissolved in 4165 mL of $dH_2O$ and mixed at a slow speed using a homogeniser. While the mixture was being stirred, 100 g glycerine was added. Myritol 318 (250 g), isopropyl myristate (25 g), Cetiol CC (75 g) and Novemer EC-1 polymer (50 g) were mixed in a separate container and then added to the main mixture, while mixing with moderate agitation. Euxyl PE 9010 was slowly added to the mixture until a uniform gel-cream was obtained. Thereafter, the ethanolic extract of *A. linearis* was added to the gel cream as set out in Table 5.

The pigmentation of the skin was measured using Mexametre MX18® at the start of the clinical study and at day 56 (end of the study).

The clinical study found that the Tested product 1 (AL100) significantly (20%) increased the mean melanin index after 56 days of product use and 88% of the subjects presented an improvement in skin repigmentation. It was found that the ethanolic extract of *A. linearis* at a concentration of 100 μg/mL in finished formulation resulted in significant repigmentation of 21% in the non-pigmented zones compared to the pigmented zones, which was observed in 88% of the volunteers in the clinical study. The overall feedback from the patients' assessments were positive, with 70% indicating that they observed repigmentation on skin lesions and 50% of the subjects agreed that the depigmented area was less visible. From the feedback, 90% indicated that they would like to continue using the product and stated that the product was pleasant. All the subjects agreed that the product penetrates their skin easily, with 60% of the subjects indicating the product is good for their skin type. The results for AL 100 were significantly better that for the group receiving the placebo.

TABLE 5

Preparation of the samples submitted to Dermscan
for clinical studies on hypopigmented patients.

| Batch | Study Number | Preparation |
|---|---|---|
| 1 | 18E1316 Placebo | Twenty-three 50 mL Falcon tubes were filled with the gel cream without the extract |
| 2 | 18E1316 Tested product 1: AL 100 | A stock was prepared by weighing off 100 mg of ethanolic extract of *A. linearis*, which was first dissolved in 20 mL EtOH to which 30 mL dH20 was added. Eleven 50 mL |

TABLE 5-continued

Preparation of the samples submitted to Dermscan
for clinical studies on hypopigmented patients.

| Batch | Study Number | Preparation |
|---|---|---|
| 3 | 18E1316 Tested product 2: AL 200 | Falcon tubes were filled with 35 g of the stock and 700 g of gel cream A stock was prepared by weighing off 200 mg of ethanolic extract of *A. linearis*, which was first dissolved in 20 mL EtOH to which 30 mL dH2O was added. Eleven 50 mL Falcon tubes were filled with 35 g of the stock and 700 g of gel cream |

Surprisingly, less significant values were observed for Tested product 2 (AL 200), which resulted in an increase of 10% in the mean melanin index after 56 days of product use. It was reported that 67% of the patients presented an improvement in skin repigmentation. The results for the two concentrations indicated that the efficacy was not linked to a dose response. A nonsignificant increase of 3% in the mean melanin index was observed for the placebo after 56 days of product use.

Although there are some cosmeceutical products which are used for repigmentation and the treatment of vitiligo, it is submitted that this is the first report of *A. linearis* resulting in repigmentation and the potential use as a treatment for hypopigmented disorders.

REFERENCES

Cardinali G., Bolasco G., Aspite N., Lucania G., Lotti L. V., Torrisi M. R., Picardo M., 2008. Melanosome transfer promoted by keratinocyte growth factor in light and dark skin-derived keratinocytes. Journal of Investigative Dermatology, 128, 3: 558-567.

Matsuda, H.; Kawaguchi, Y.; Yamazaki, M.; Hirata, N.; Naruto, S.; Asanuma, Y.; Kaihatsu, T.; Kubo, M. Melanogenesis stimulation in murine B16 melanoma cells by *Piper nigrum* leaf extract and its lignan constituents. Biological and Pharmaceutical Bulletin. 2004, 27, 1611-1616.

Mortelmans, K., Zeiger, E., The Ames *Salmonella*/microsome mutagenicity assay, Mutat. Res., 455 (2000) 29-60.

Purves, D., Harvey, C., Tweats, D., Lumley, C. E., Genotoxicity testing: current practices and strategies used by the pharmaceutical industry, Mutagenesis, 10 (1995) 297-312.

Van der Merwe, J., Joubert, E., Richards, E., Manley, M., Snijman, P., Marnewick, J. L., Gelderblom, W., A comparative study on the antimutagenic properties of aqueous extracts of *Aspalathus linearis* (Rooibos), different *Cyclopia* spp. (honeybush) and *Camellia sinensis* teas, Mutat. Res., 611 (2006) 42-53.

The invention claimed is:

1. A method of preventing or treating a hypopigmentary disorder of skin in a subject comprising applying a topical composition to the skin of the subject, wherein the topical composition comprises:
   a) a 100 µg/mL ethanolic extract from the plant *Aspalathus linearis;*
   b) acrylates/$C_{10-30}$ alkyl acrylate crosspolymer;
   c) glycerin;
   d) caprylic/capric triglyceride;
   e) isopropyl myristate;
   f) dicaprylyl carbonate;

g) acrylate/acrylamide copolymer dispersed in oil and polysorbate-85;
   h) a phenoxyethanol and ethylhexylglycerin preservative blend;
   i) water; and
   j) a dermatologically acceptable carrier.

2. The method of claim 1, wherein the ethanolic extract from the plant *Aspalathus linearis* is a crude extract.

3. The method of claim 1, wherein the topical composition is a lotion, cream, gel, serum, or emulsion.

4. The method of claim 1, wherein the topical composition comprises one or more additive selected from the group consisting of a rheology modifier, a suspending agent, a thickener, a denaturant, a humectant, a solvent, an emollient, an emulsifier and/or a preservative.

5. The method of claim 1, wherein the topical composition comprises:
   a) 100 µg/mL crude ethanolic extract from the plant *Aspalathus linearis;*
   b) 1 to 10 mg/mL acrylates/$C_{10-30}$ alkyl acrylate crosspolymer;
   c) 10 to 50 mg/mL glycerin;
   d) 25 to 100 mg/mL caprylic/capric triglyceride;
   e) 5 to 50 mg/mL isopropyl myristate;
   f) 5 to 50 mg/mL dicaprylyl carbonate;
   g) 5 to 15 mg/mL acrylate/acrylamide copolymer dispersed in oil and polysorbate-85;
   h) 5 to 15 mg/mL a phenoxyethanol and ethylhexylglycerin preservative blend; and
   i) water.

6. The method of claim 1, wherein the hypopigmentary disorder is selected from the group consisting of idiopathic guttate hypomelanosis, *Pityriasis alba*, progressive macular hypomelanosis, post-inflammatory hypopigmentation, leukoderma, vitiligo and hypopigmented scarring.

7. The method of claim 1, wherein the topical composition stimulates melanin production and/or melanin transfer.

8. A topical composition comprising:
   a) a 100 µg/mL ethanolic extract from the plant *Aspalathus linearis;*
   b) acrylates/$C_{10-30}$ alkyl acrylate crosspolymer;
   c) glycerin;
   d) caprylic/capric triglyceride
   e) isopropyl myristate;
   f) dicaprylyl carbonate;
   g) acrylate/acrylamide copolymer dispersed in oil and polysorbate-85;
   h) a phenoxyethanol and ethylhexylglycerin preservative blend;
   i) water; and
   j) a dermatologically acceptable carrier.

9. The topical composition of claim 8, wherein the ethanolic extract from the plant *Aspalathus linearis* is a crude extract.

10. The topical composition of claim 8, wherein the topical composition is a lotion, cream, gel, serum, or emulsion.

11. The topical composition of claim 8, wherein the topical composition comprises one or more additive selected from the group consisting of a rheology modifier, a suspending agent, a thickener, a denaturant, a humectant, a solvent, an emollient, an emulsifier and/or a preservative.

12. The topical composition of claim 8, wherein the topical composition comprises:

a) 100 μg/mL crude ethanolic extract from the plant *Aspalathus linearis;* b) 1 to 10 mg/mL acrylates/$C_{10-30}$ alkyl acrylate crosspolymer;

c) 10 to 50 mg/mL glycerin;

d) 25 to 100 mg/mL caprylic/capric triglyceride;

e) 5 to 50 mg/mL isopropyl myristate;

f) 5 to 50 mg/mL dicaprylyl carbonate;

g) 5 to 15 mg/mL acrylate/acrylamide copolymer dispersed in oil and polysorbate-85;

h) 5 to 15 mg/mL a phenoxyethanol and ethylhexylglycerin preservative blend; and i) water.

* * * * *